(12) United States Patent
Chuter et al.

(10) Patent No.: US 8,728,145 B2
(45) Date of Patent: May 20, 2014

(54) LOW PROFILE NON-SYMMETRICAL STENTS AND STENT-GRAFTS

(75) Inventors: Timothy A. M. Chuter, San Francisco, CA (US); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/335,142

(22) Filed: Dec. 22, 2011

(65) Prior Publication Data

US 2012/0130479 A1    May 24, 2012

Related U.S. Application Data

(63) Continuation-in-part of application No. 12/622,351, filed on Nov. 19, 2009, which is a continuation of application No. 12/472,082, filed on May 26, 2009, now Pat. No. 8,574,284, which is a continuation-in-part of application No. 12/332,904, filed on Dec. 11, 2008.

(60) Provisional application No. 61/016,753, filed on Dec. 26, 2007.

(51) Int. Cl.
    *A61F 2/06*    (2013.01)

(52) U.S. Cl.
    USPC ............ 623/1.13; 623/1.15; 623/1.31

(58) Field of Classification Search
    CPC ....... A61F 2/04; A61F 2/07; A61F 2002/072; A61F 2002/075; A61F 2/82; A61F 2/821; A61F 2002/91533; A61F 2002/9154

USPC ............ 623/1.31, 1.35, 1.26, 2.2, 2.14, 623/2.17–2.18, 900
See application file for complete search history.

(56) References Cited

U.S. PATENT DOCUMENTS

| | | |
|---|---|---|
| 5,258,021 A | 11/1993 | Duran |
| 5,569,295 A | 10/1996 | Lam |
| 5,843,164 A | 12/1998 | Frantzen et al. |
| 5,913,897 A | 6/1999 | Corso et al. |
| 6,071,307 A | 6/2000 | Rhee et al. |
| 6,296,662 B1 | 10/2001 | Caffey |

(Continued)

FOREIGN PATENT DOCUMENTS

EP    0960607    12/1999

OTHER PUBLICATIONS

Office Action for U.S. Appl. No. 12/332,904 dated Oct. 4, 2010, 9 pgs.

(Continued)

*Primary Examiner* — Andrew Iwamaye
*Assistant Examiner* — Leslie Coburn
(74) *Attorney, Agent, or Firm* — Brinks Gilson & Lione

(57) ABSTRACT

Various stents and stent-graft systems for treatment of medical conditions are disclosed. In one embodiment, an exemplary stent-graft comprises first and second stents, which each may comprise a series of distal apices disposed distal to a proximal end of the graft, and a series of proximal apices disposed proximally beyond the proximal end of the graft. In one example, the first stent comprises a first uniform segment, and the second stent comprises a second uniform wire segment, where the first uniform segment comprises portions disposed both internal and external to the second uniform wire segment.

20 Claims, 12 Drawing Sheets

(56) References Cited

U.S. PATENT DOCUMENTS

| | | | |
|---|---|---|---|
| 6,348,068 B1 | 2/2002 | Campbell et al. | |
| 6,368,345 B1 | 4/2002 | Dehdashtian et al. | |
| 6,423,090 B1 | 7/2002 | Hancock | |
| 6,539,984 B2 | 4/2003 | Lam | |
| 6,551,350 B1* | 4/2003 | Thornton et al. | 623/1.13 |
| 6,582,458 B1 | 6/2003 | White et al. | |
| 6,616,689 B1 | 9/2003 | Ainsworth et al. | |
| 6,629,994 B2 | 10/2003 | Gomez et al. | |
| 6,635,083 B1 | 10/2003 | Cheng et al. | |
| 6,645,242 B1 | 11/2003 | Quinn | |
| 6,648,911 B1 | 11/2003 | Sirhan et al. | |
| 6,849,088 B2 | 2/2005 | Dehdashtian et al. | |
| 6,962,604 B2 | 11/2005 | Hijlkema | |
| 7,186,263 B2 | 3/2007 | Golds et al. | |
| 7,341,598 B2 | 3/2008 | Davidson et al. | |
| 7,407,509 B2 | 8/2008 | Greenberg et al. | |
| 7,473,275 B2 | 1/2009 | Marquez | |
| 2002/0022877 A1 | 2/2002 | Mueller et al. | |
| 2003/0033003 A1 | 2/2003 | Harrison et al. | |
| 2003/0088305 A1 | 5/2003 | Van Schie et al. | |
| 2003/0125797 A1 | 7/2003 | Chobotov et al. | |
| 2003/0130720 A1 | 7/2003 | DePalma et al. | |
| 2003/0199967 A1 | 10/2003 | Hartley et al. | |
| 2004/0117003 A1 | 6/2004 | Ouriel et al. | |
| 2004/0117004 A1 | 6/2004 | Osborne et al. | |
| 2004/0176833 A1* | 9/2004 | Pavcnik et al. | 623/1.13 |
| 2004/0215316 A1 | 10/2004 | Smalling | |
| 2004/0254625 A1 | 12/2004 | Stephens et al. | |
| 2005/0033406 A1 | 2/2005 | Barnhart et al. | |
| 2005/0049674 A1* | 3/2005 | Berra et al. | 623/1.13 |
| 2005/0075730 A1* | 4/2005 | Myers et al. | 623/2.18 |
| 2005/0102022 A1* | 5/2005 | Solovay et al. | 623/1.13 |
| 2005/0113905 A1 | 5/2005 | Greenberg et al. | |
| 2005/0131516 A1 | 6/2005 | Greenhalgh | |
| 2005/0154446 A1 | 7/2005 | Phillips et al. | |
| 2005/0222671 A1 | 10/2005 | Schaeffer et al. | |
| 2005/0273155 A1 | 12/2005 | Bahler et al. | |
| 2006/0052860 A1 | 3/2006 | Gomez et al. | |
| 2006/0100695 A1 | 5/2006 | Peacock, III et al. | |
| 2006/0190075 A1 | 8/2006 | Jordan et al. | |
| 2006/0247761 A1 | 11/2006 | Greenberg et al. | |
| 2006/0267247 A1 | 11/2006 | Anukhin et al. | |
| 2007/0027525 A1 | 2/2007 | Ben-Muvhar | |
| 2007/0067016 A1 | 3/2007 | Jung | |
| 2007/0073388 A1 | 3/2007 | Krolik et al. | |
| 2007/0100427 A1* | 5/2007 | Perouse | 623/1.11 |
| 2007/0135889 A1 | 6/2007 | Moore et al. | |
| 2007/0168019 A1 | 7/2007 | Amplatz et al. | |
| 2007/0179592 A1 | 8/2007 | Schaeffer | |
| 2007/0191927 A1 | 8/2007 | Bowe et al. | |
| 2007/0203566 A1 | 8/2007 | Arbefeuille et al. | |
| 2007/0208256 A1 | 9/2007 | Marilla | |
| 2007/0225797 A1 | 9/2007 | Krivoruhko | |
| 2007/0233220 A1 | 10/2007 | Greenan | |
| 2007/0244547 A1 | 10/2007 | Greenan | |
| 2007/0250152 A1 | 10/2007 | Xiao et al. | |
| 2007/0282433 A1 | 12/2007 | Limon et al. | |
| 2008/0086190 A1 | 4/2008 | Ta | |
| 2008/0109066 A1 | 5/2008 | Quinn | |
| 2008/0119943 A1 | 5/2008 | Armstrong | |
| 2008/0269866 A1 | 10/2008 | Hamer et al. | |
| 2008/0281399 A1 | 11/2008 | Hartley et al. | |
| 2008/0319534 A1 | 12/2008 | Birdsall et al. | |
| 2009/0005856 A1 | 1/2009 | Pappas et al. | |
| 2009/0043376 A1 | 2/2009 | Hamer et al. | |
| 2009/0048663 A1 | 2/2009 | Greenberg | |
| 2009/0105809 A1 | 4/2009 | Lee et al. | |
| 2009/0171437 A1 | 7/2009 | Brocker et al. | |

OTHER PUBLICATIONS

Response to Office Action for U.S. Appl. No. 12/332,904 filed Mar. 4, 2011, 10 pgs.
Final Office Action for U.S. Appl. No. 12/332,904 dated May 9, 2011, 11 pgs.
Notice of Appeal U.S. Appl. No. 12/332,904 dated Nov. 7, 2011, 1 pg.
Applicants' Interview Agenda for U.S. Appl. No. 12/332,904 dated Nov. 10, 2011, 2 pgs.
Examiner's Interview Summary for U.S. Appl. No. 12/332,904 dated Nov. 10, 2011, 3 pgs.
Office Action for U.S. Appl. No. 12/332,904 dated Nov. 18, 2011, 12 pgs.
Applicants' Interview Summary for U.S. Appl. No. 12/332,904 dated Jan. 24, 2012, 2 pgs.
Response to Office Action for U.S. Appl. No. 12/332,904 dated Feb. 21, 2012, 9 pgs.
Final Office Action for U.S. Appl. No. 12/332,904 dated Jan. 3, 2013, 5 pgs.
RCE for U.S. Appl. No. 12/332,904 dated Jul. 2, 2013, 14 pgs.
Office Action for U.S. Appl. No. 12/472,082 dated Oct. 4, 2010, 9 pgs.
Examiner's Interview Summary for U.S. Appl. No. 12/472,082 dated Jan. 25, 2011, 3 pgs.
Response to Office Action for U.S. Appl. No. 12/472,082 filed Mar. 4, 2011, 11 pgs.
Office Action for U.S. Appl. No. 12/472,082 dated Jun. 2, 2011, 13 pgs.
Applicants' Interview Agenda for U.S. Appl. No. 12/472,082 dated Nov. 9, 2011, 2 pgs.
Examiner's Interview Summary for U.S. Appl. No. 12/472,082 dated Nov. 9, 2011, 3 pgs.
Office Action for U.S. Appl. No. 12/472,082 dated Dec. 2, 2011, 14 pgs.
Applicants' Interview Summary for U.S. Appl. No. 12/472,082 dated Jan. 24, 2012, 2 pgs.
Response to Office Action for U.S. Appl. No. 12/472,082 dated Apr. 17, 2012, 10 pgs.
Final Office Action for U.S. Appl. No. 12/472,082 dated Sep. 13, 2012, 15 pgs.
Applicant Summary of Interview for U.S. Appl. No. 12/472,082 dated Feb. 11, 2013, 2 pgs.
Response to Final Office Action for U.S. Appl. No. 12/472,082 dated Mar. 4, 2013, 9 pgs.
Applicant Initiated Interview Summary for U.S. Appl. No. 12/472,082 dated Mar. 5, 2013, 3 pgs.
Request for Continued Examination for U.S. Appl. No. 12/472,082 dated Mar. 12, 2013, 5 pgs.
Notice of Allowance for U.S. Appl. No. 12/472,082 dated Jun. 21, 2013, 14 pgs.
Notice of Allowance for U.S. Appl. No. 12/472,082 dated Aug. 14, 2013, 5 pgs.
Request Under Rule 48 Correcting Inventorship for U.S. Appl. No. 12/472,082 dated Aug. 30, 2013, 41 pgs.
Request for Correction of Filing Receipt for U.S. Appl. No. 12/472,082 dated Sep. 16, 2013, 23 pgs.
Response to Request for Correction of Filing Receipt for U.S. Appl. No. 12/472,082 dated Sep. 17, 2013, 1 pg.
Issue Fee Payment for U.S. Appl. No. 12/472,082 dated Sep. 19, 2013, 2 pgs.
Issue Notification for U.S. Appl. No. 12/472,082 dated Oct. 16, 2013, 1 pg.
Office Action for U.S. Appl. No. 12/622,351 dated Oct. 6, 2010, 11 pgs.
Examiner's Interview Summary for U.S. Appl. No. 12/622,351 dated Jan. 25, 2011, 3 pgs.
Response to Office Action for U.S. Appl. No. 12/622,351 filed Mar. 9, 2011, 12 pgs.
Final Office Action for U.S. Appl. No. 12/622,351 dated Jun. 10, 2011, 12 pgs.
Interview Agenda for U.S. Appl. No. 12/622,351 dated Nov. 10, 2011, 2 pgs.
Examiner's Interview Summary for U.S. Appl. No. 12/622,351 dated Nov. 10, 2011, 6 pgs.
Office Action for U.S. Appl. No. 12/622,351 dated Dec. 1, 2011, 16 pgs.
Applicants' Interview Summary for U.S. Appl. No. 12/622,351 dated Jan. 24, 2012, 2 pgs.

(56) References Cited

OTHER PUBLICATIONS

Response to Office Action for U.S. Appl. No. 12/622,351 dated Apr. 17, 2012, 14 pgs.
Final Office Action for U.S. Appl. No. 12/622,351 dated Jun. 10, 2012, 12 pgs.
Letter Requesting Interview with Examiner for U.S. Appl. No. 12/622,351 dated Nov. 2, 2012, 1 pg.
Interview Summary and Appendix for U.S. Appl. No. 12/622,351 dated Nov. 8, 2012, 4 pgs.
Response to Office Action for U.S. Appl. No. 12/622,351 dated Dec. 26, 2012, 10 pgs.
Office Action for U.S. Appl. No. 12/622,351 dated Apr. 3, 2013, 29 pgs.
Applicant Initiated Interview Summary for U.S. Appl. No. 12/622,351 dated Jun. 11, 2013, 4 pgs.
Follow Up Interview Summary for U.S. Appl. No. 12/622,351 dated Jun. 19, 2013, 4 pgs.
Response to Office Action for U.S. Appl. No. 12/622,351 dated Jul. 3, 2013, 14 pgs.
Terminal Disclaimer for U.S. Appl. No. 12/622,351 dated Aug. 28, 2013, 6 pgs.
Terminal Disclaimer Decision for U.S. Appl. No. 12/622,351 dated Aug. 29, 2013, 1 pg.
Notice of Allowance for U.S. Appl. No. 12/622,351 dated Sep. 4, 2013, 9 pgs.
Notice to File Corrected Application Papers for U.S. Appl. No. 12/622,351 dated Sep. 17, 2013, 3 pgs.
Response to Notice to File Corrected Application Papers for U.S. Appl. No. 12/622,351 dated Sep. 20, 2013, 3 pgs.
Response to Rule 312 Amendment for U.S. Appl. No. 12/622,351 dated Oct. 4, 2013, 2 pgs.
Acknowledgement of Receipt of Priority Document for U.S. Appl. No. 12/622,351 dated Oct. 15, 2013, 1 pg.
A127 Extended European Search Report for 12275202 dated Apr. 9, 2013, 8 pgs.

\* cited by examiner

LOW PROFILE NON-SYMMETRICAL STENTS AND STENT-GRAFTS

CROSS-REFERENCE TO RELATED APPLICATIONS

This application is a continuation-in-part of U.S. Utility patent application Ser. No. 12/622,351, filed Nov. 19, 2009 and entitled "Low Profile Non-Symmetrical Stent," which is a continuation of U.S. patent application Ser. No. 12/472,082, filed May 26, 2009, which is a continuation-in-part of U.S. patent application Ser. No. 12/332,904, filed Dec. 11, 2008, which claims priority to U.S. Provisional Application Ser. No. 61/016,753, filed Dec. 26, 2007, and also claims priority under 35 U.S.C. §119 to Great Britain Patent Application No. GB0920235.9, filed Nov. 18, 2009 and Great Britain Patent Application No. GB0920327.4, filed Nov. 19, 2009, each of which is incorporated herein by reference in its entirety.

BACKGROUND

The present embodiments relate generally to stents and stent-grafts for use in body vessels to treat medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Various existing self-expanding and balloon-expandable stent designs and configurations comprise generally symmetrical end regions including one or more apices formed of nitinol or another alloy wire formed into a ring. The apices commonly comprise relatively acute bends or present somewhat pointed surfaces, which may facilitate compression of the stent to a relatively small delivery profile due to the tight bend of the apices. Although having this advantage, in some situations, such relatively acute or pointed apices may be undesirable, in particular in vessel anatomies that are curved or tortuous such as, for example, the thoracic aorta.

The thoracic aorta presents a challenging anatomy for stent grafts used to treat thoracic aneurysms or dissections. The thoracic aorta comprises a curve known as the aortic arch, which extends between the ascending thoracic aorta (closet to the heart) and the descending thoracic aorta (which extends toward the abdominal aorta). Thoracic stent grafts are used to exclude thoracic aortic aneurysms. A stent graft's ability to conform to the tortuous anatomy of the aortic arch is a major concern. Current designs sometimes lack the desired sealing ability at the proximal end of the stent graft (closest to the heart). Also, current thoracic devices present a relatively large profile which, with some patients' anatomies may be problematic. Finally, many current stents have relatively acute points that may prevent them from being used in the aortic arch for fear of undesirable interaction with the artery wall after an extended amount of time in the patient.

Therefore, a generally nonsymmetrical stent having at least one relatively rounded apex that is less invasive in an expanded state than stents with more acute apices may alleviate the above problems, while providing an improved compliance to the aortic arch and increased radial force if used as a sealing and/or alignment stent, as well as a desirable ability to be crimped to a readily introducible diameter.

As one particular example, type-A thoracic aortic dissection (TAD-A) is a condition in which the intimal layer of the ascending thoracic aorta develops a tear, allowing blood to flow into the layers of the aortic wall, causing the development of a medial or subintimal hematoma. TAD-A is associated with a strikingly high mortality rate (about one-fourth to one-half of victims die within the first 24-48 hours). The only current treatment for TAD-A is open surgery, where the chest is opened, the aorta is clamped, and a vascular prosthesis is sewn in place. Operative mortality rate for this procedure may be around 10%. Endovascular treatment of TAD-B (which affects the descending thoracic aorta) has been effective in reducing short-term and longer term mortality. Therefore, it is desirable to provide an endovascular device configured to address the anatomic challenges of the thoracic aorta.

SUMMARY

Various stents and stent-grafts for treatment of medical conditions are disclosed. In one embodiment, a stent-graft comprises a graft and first and second stents. The first stent comprises a plurality of proximal apices, a plurality of distal apices, and a plurality of generally straight portions disposed between the plurality of proximal and distal apices. The second stent comprises a plurality of proximal apices, a plurality of distal apices, and a plurality of generally straight portions disposed between the plurality of proximal and distal apices.

In one embodiment, the series of distal apices of the first stent are each disposed distal to the proximal end of the graft, and the series of proximal apices of the first stent are each disposed proximally beyond the proximal end of the graft. Additionally, the series of distal apices of the second stent are each disposed distal to the proximal end of the graft, and the series of proximal apices of the second stent are each disposed proximally beyond the proximal end of the graft.

The first stent may comprise a first uniform segment, and the second stent may comprise a second uniform wire segment. In one example, the first uniform segment comprises portions disposed both internal and external to the second uniform wire segment.

In one embodiment, each of the proximal apices of the first stent may be circumferentially offset from each of the proximal apices of the second stent. Further, each of the distal apices of the first stent may be circumferentially offset from each of the distal apices of the second stent.

In one exemplary embodiment, the first stent and the second stent comprise identical geometries. At least one distal apex of the first stent may comprise a first curved portion having a first radius of curvature, and at least one proximal apex of the first stent may comprise a second curved portion having a second radius of curvature, where the second radius of curvature is greater than the first radius of curvature. Similarly, at least one distal apex of the second stent comprises a third curved portion having a third radius of curvature, and at least one proximal apex of the second stent comprises a fourth curved portion having a fourth radius of curvature, where the fourth radius of curvature is greater than the third radius of curvature.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

The present embodiments relate generally to stents and stent-grafts for use in body vessels to treat medical conditions. In particular, the embodiments relate to a novel asymmetric stent having opposing sets of curved apices, where the curved section of one set of apices has a radius of curvature that is greater than the curved section of the other set of apices, and may present a lower profile than conventional stents. The lower profile may present advantages for use in patients with particularly tortuous or small-diameter vessels.

In the present application, the term "proximal" refers to a direction that is generally closest to the heart during a medical procedure, while the term "distal" refers to a direction to that is furthest from the heart during a medical procedure. Reference throughout is made to proximal and distal apices, but those of skill in the art will appreciate that the proximal-distal orientation of stents of the present invention may be reversed without exceeding the scope of the present invention.

As shown in FIGS. 4-15, this novel stent is not symmetrical like many commercially available stents, in that the radius of curvature of the opposing proximal and distal apices is different between the top and bottom of the stent. The stents may be attached to either end of a stent graft to provide sealing and may be used internally or externally to the graft material to provide support to the graft.

The asymmetric stent may be configured such that, when used with a graft, it will provide a sufficiently strong radial force at the graft's end openings to hold the graft material open against the artery wall. Also, the stent is intended to be short in length so that the graft will include flexibility sufficient to accommodate a patient's anatomy. This combination of flexibility and strong radial force provides an improved seal between the graft and artery wall. In addition, enhanced flexibility is provided as well, particularly when one or more stents are used to provide short segments and better accommodate curves.

Figure 1:
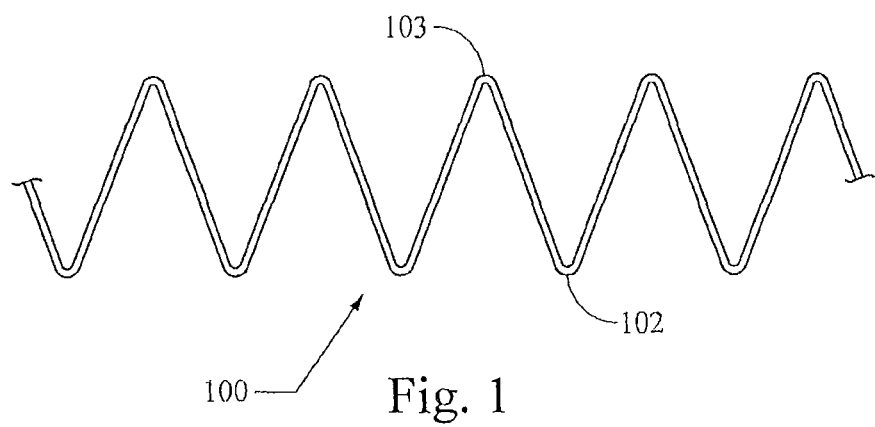
FIGS. 1-3 show different views of a symmetrical stent.
Figure 2:
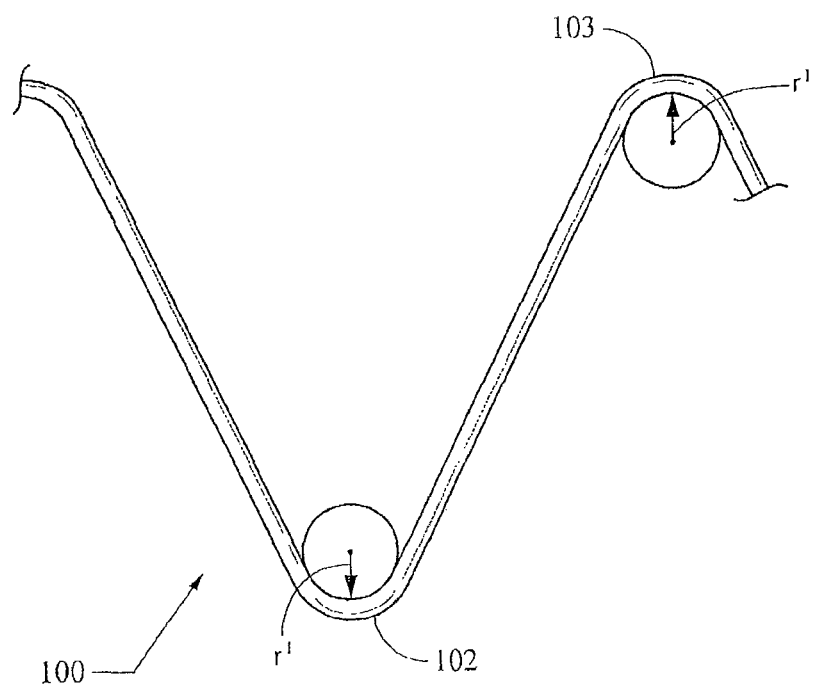
Figure 3:
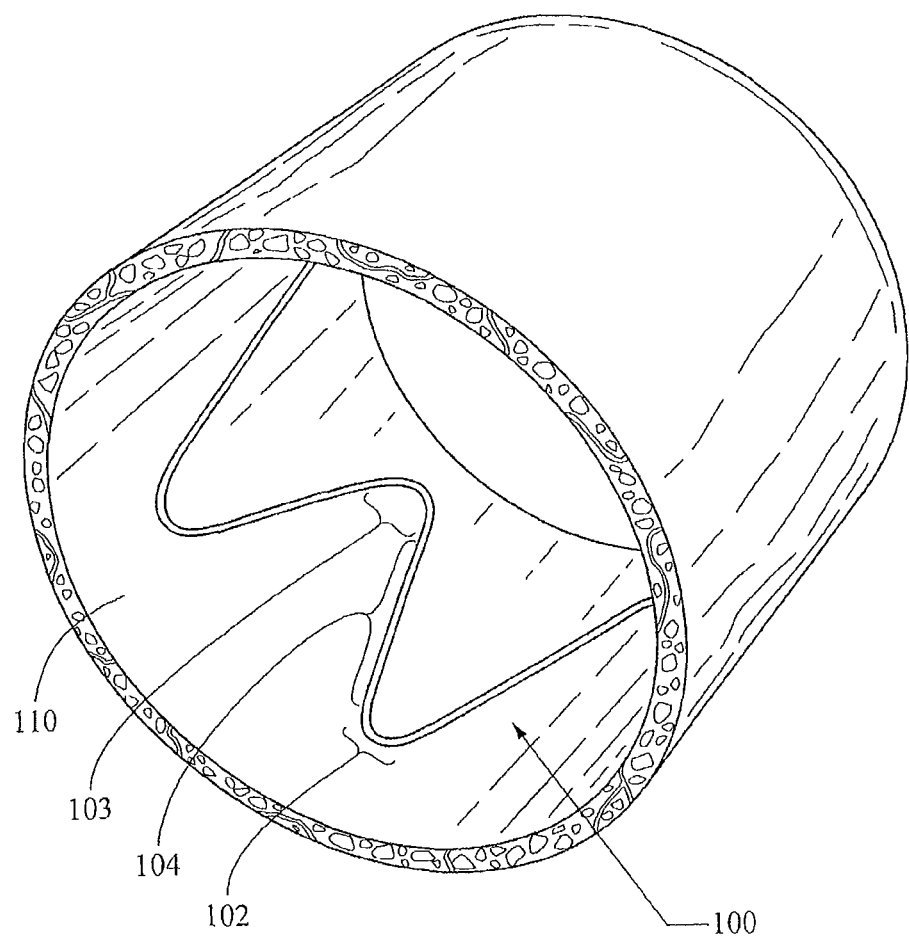

FIG. 1 shows a conventional stent 100, which has symmetrical apices 102, 103. Specifically, the proximal apices 102 and the distal apices 103 all have generally the same radii of curvature ($r^1$), which is illustrated in graphic form in FIG. 2. FIG. 3 is adapted from an FEA contour simulation and shows the stent 100 in a simulated artery 110, where the stent 100 is 20% oversized. The proximal and distal apices 102, 103 (circled) exert little or no pressure against the artery wall 110, while an intermediate region 107 exerts a higher pressure to provide—in one example—a total radial sealing force of 0.178 lbf. This configuration may be crimped to 18 Fr (e.g., for introduction via a catheter), with a maximum bend strain in the apices 102, 103 of about 5.8%. When using, for example, a typical NiTi wire for the stent, it is desirable not to exceed 10-12% strain to avoid increased risk of deforming the wire or adversely affecting its durability.

FIGS. 4-7 show a first example of a non-symmetrical stent 200, which is formed as a wire ring that has non-symmetrical proximal and distal generally curved apex portions (apices) 202, 203 separated from each other by intermediate generally straight portions. Specifically, the distal apices 203 all have generally the same radii of curvature ($r^d$) as each other, but the distal apices' radii of curvature are different from those of the proximal apices 202 ($r^p$). The distal apices 203 (which may be attached to stent-grafts as described below) are generally narrowly rounded in a manner not dissimilar from a traditional z-stent, but the proximal apices 202 are more broadly rounded. The difference in the proximal and distal apices 202, 203 is illustrated in graphic form in FIG. 5. In the illustrated example, the rounded proximal apices 202 have a radius of curvature of 6.0 mm, while the narrower distal apices 202 have a radius of curvature of 1.0 mm. In certain examples of non-symmetrical stents, the radius of curvature of the rounded proximal apices (measured in the manner shown in FIG. 5) may be from about 4 mm to about 9 mm, and the radius of curvature of the narrower distal apices may be from about 0.5 mm to about 1.5 mm.

In these and other examples, the ratio of the proximal apices' radius of curvature to the distal apices' radius of curvature may be about 2.6:1 to about 18:1, and desirably may be about 6:1. The outer circumference of the stent 200 preferably is generally consistent such that, in this configuration, a solid outer face around the stent 200 would form a cylinder, although the stent will most preferably provide compliance with a surface less smooth than a cylinder.

Figure 6:
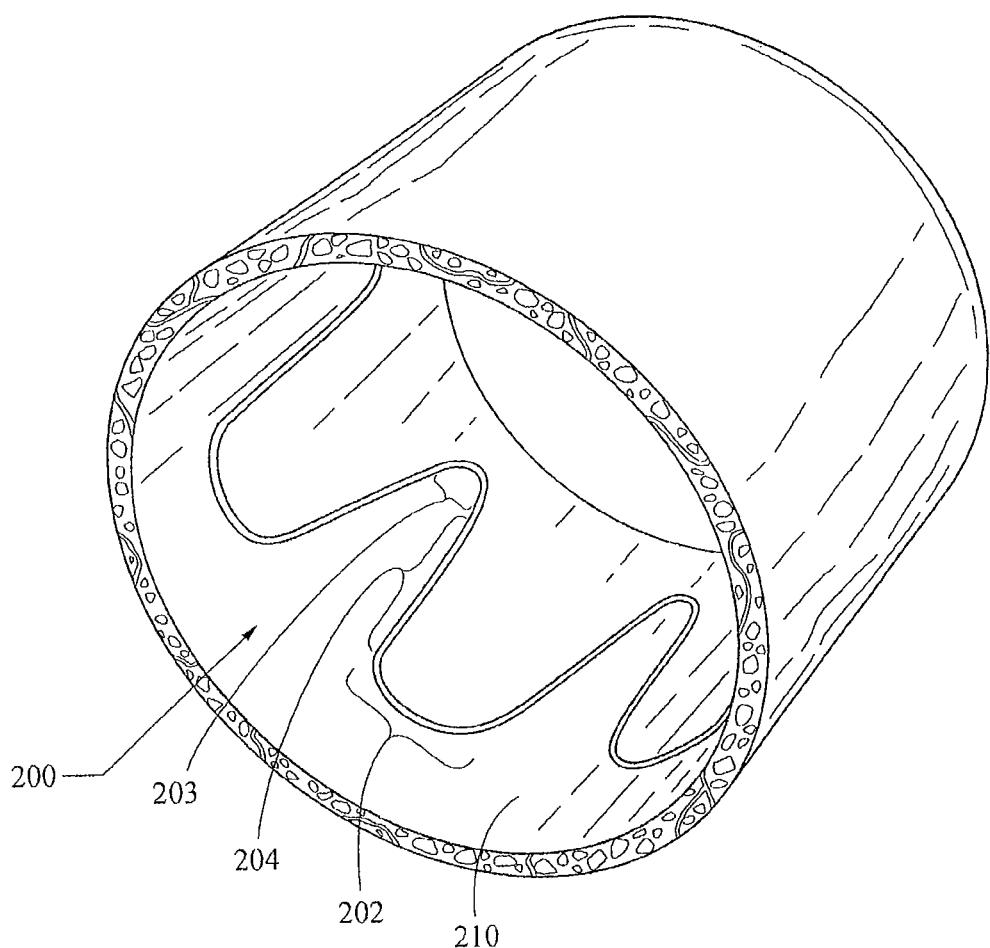
FIG. 6 shows the stent of FIG. 4 in a simulated artery.

FIG. 6 is adapted from an FEA contour simulation and shows the stent 200 in a simulated artery 210, where the stent 200 is 20% oversized. The proximal and distal apices 202, 203 (circled) exert little or no pressure against the artery wall 210, while an intermediate region 204 (boxed) exerts a greater pressure to provide—in the illustrated example—a total radial sealing force of about 0.160 lbf. This configuration may be crimped to 18 Fr, with a maximum bend strain in the apices 202, 203 of about 6.5%.

Figure 4:
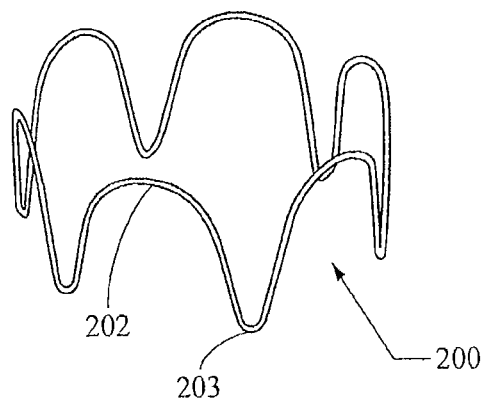
FIG. 4 depicts an example of an asymmetric stent.
Figure 5:
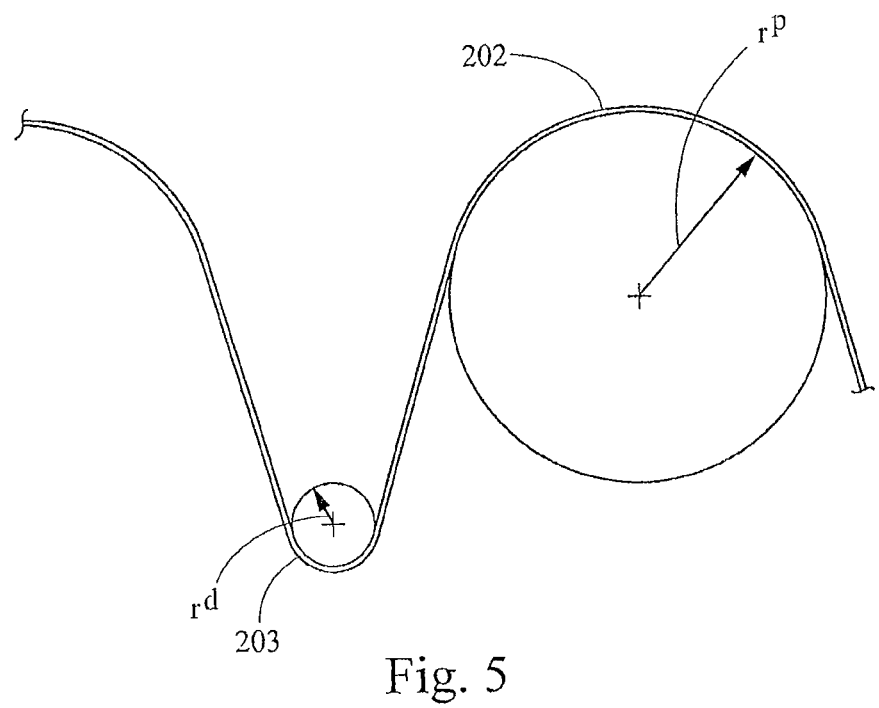
FIG. 5 diagrammatically illustrates the asymmetrical radii of curvature of the stent of FIG. 4.
Figure 7:
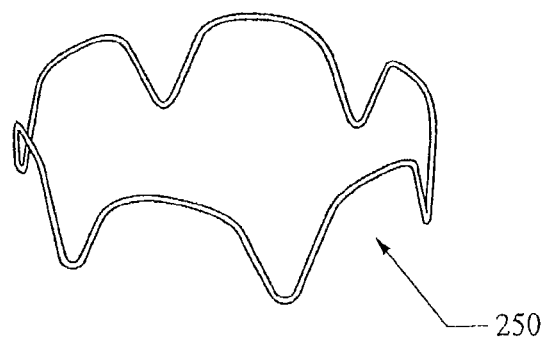
FIG. 7 depicts another example of an asymmetric stent.

FIG. 7 shows another non-symmetrical stent embodiment 250 that is very similar to the embodiment of FIGS. 4-6, but which has a shorter proximal-distal length. Each of the examples shown in FIGS. 4-7 may be manufactured in substantially the same manner as current z-stents, with a modification only of forming the proximal apices to include a greater radius of curvature than the distal apices.

Figure 8:
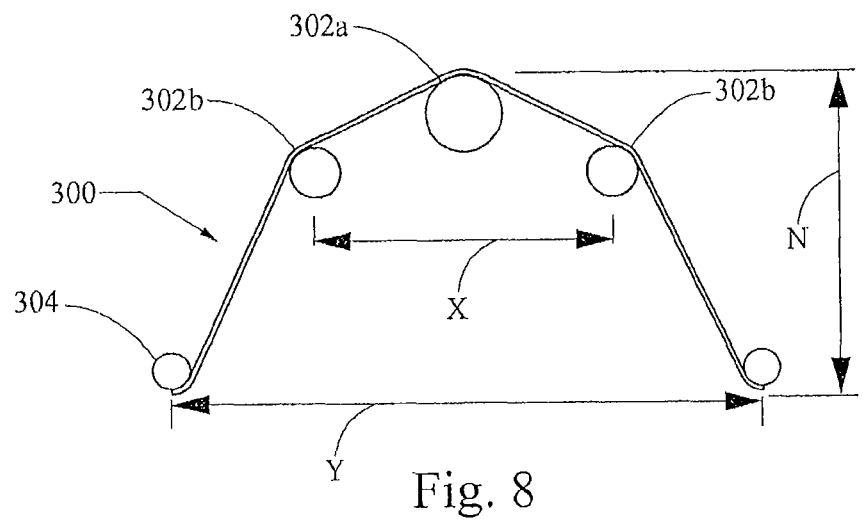
FIG. 8 diagrammatically illustrates the asymmetrical radii of curvature of yet another example of a stent.
Figure 9:
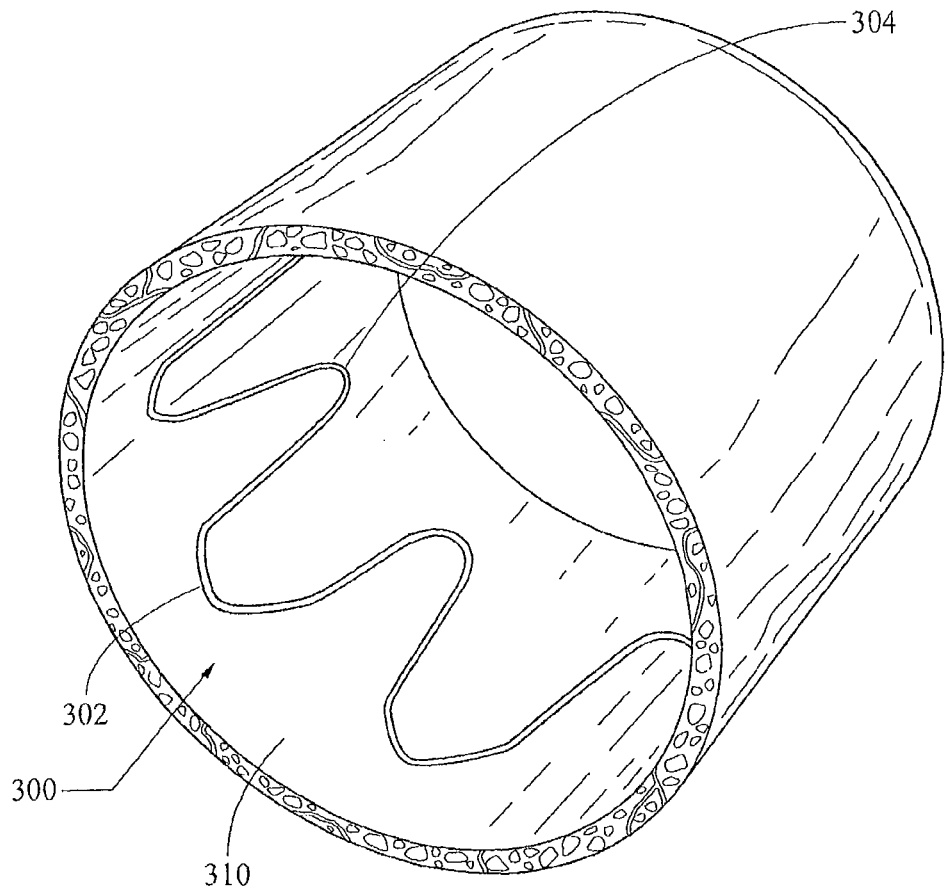
FIG. 9 shows the stent of FIG. 8 in a simulated artery.

FIGS. 8-9 illustrate another example of a non-symmetrical stent 300, which has a proximal "rounded roof shape" profile rather than the generally semicircular profile of the examples described above with reference to FIGS. 4-7. The profile of each proximal apex 302 includes a central fillet 302a and a pair of symmetrically opposed shoulder fillets 302b that may be generally equidistant from the central fillet 302a, or that may be disposed at varied distances therefrom. For the proximal apices of the stent 300, the central fillets 302a each have a radius of curvature of 1.0 mm, and the shoulder fillets 302b each have a fillet radius of curvature of 0.5 mm. The distal apices 304 have a radius of curvature of 1.0 mm. In another example having the rounded roof shape configuration (not shown), the central and shoulder fillets of proximal apices may each have the same radius of curvature such as, for example, 0.5 mm each, with distal apices also having a 0.5 mm radius of curvature. In other examples, the central and shoulder fillets 302a, 302b may each have a radius of curvature from about 0.5 mm to about 5 mm, and the distal apices may each have a radius of curvature of about 0.5 mm to about 1.5 mm. In another example having the rounded roof shape configuration (not shown), the ratio between the radii of curvature of the central and each shoulder fillet of the proximal apices may be about 3:1. FIG. 8 also shows three spans useful for describing desirable proportions in stent embodiments: "x" indicates the distance between the apical extremities of the shoulder fillets 302b, "y" indicates the distance between the tips of the distal apices 304, and "z" indicates the distance along a longitudinal axis between the tip of the distal apices 304 and the apical extremity of the proximal fillet 302a. Desirable embodiments may include an x:y ratio of about 1:3 to about 7:8 and a y:z ratio of about 1:1 to about 3:1. In yet another example (not shown), the filleted apices of this example may be combined with the generally semicircular apices of the example described with reference to FIGS. 4-7.

FIG. 9 is adapted from an FEA contour simulation and shows the stent 300 in a simulated artery 310, where the stent 300 is 20% oversized. The proximal and distal apices 302, 304 exert little or no pressure against the artery wall 310, while an intermediate region exerts a greater pressure to provide—in the illustrated example—a total radial sealing force of about 0.420 lbf. This configuration may be crimped to 18 Fr, with maximum bend strains in the apices that may be less than about 9% and preferably are less than about 10-12%. The greater radial sealing force of this example may provide advantages for stent placement and retention in certain circumstances as compared to existing z-stents.

Figure 10:
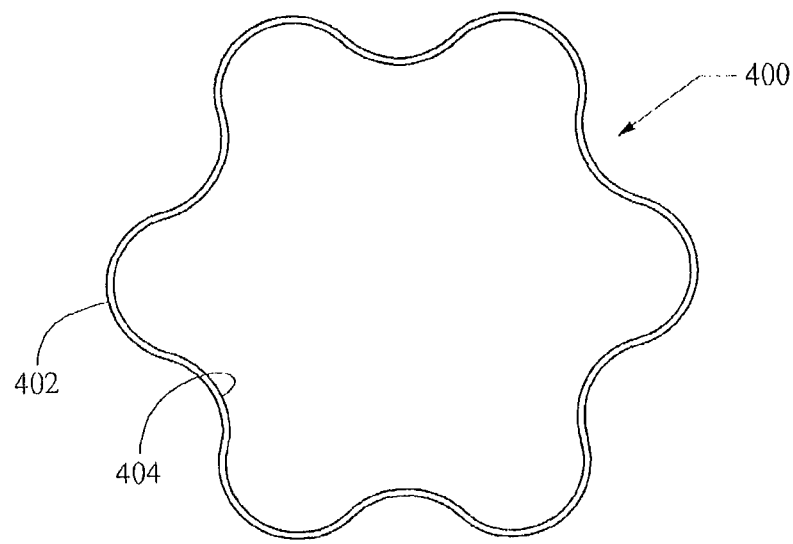
FIG. 10 shows an end view of still another example of an asymmetric stent.
Figure 11:
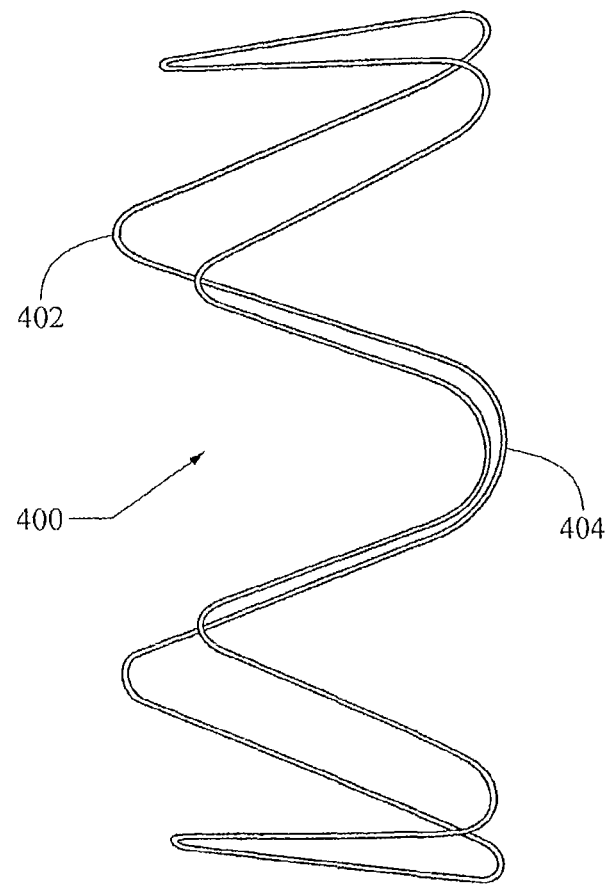
FIG. 11 shows a side view of the stent of FIG. 10.
Figure 12:
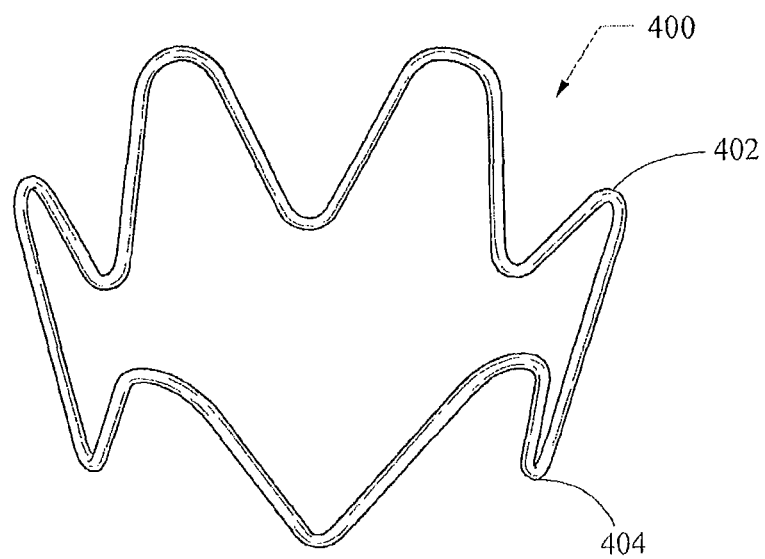
FIG. 12 is a top perspective view of the stent of FIG. 10.

FIGS. 10-13 illustrate another example of a non-symmetrical stent 400, which has an expanded "flower configuration" as shown in FIG. 10. Specifically, when the stent 400 is in an expanded configuration, the circumference around the proximal more-rounded apices 402 is greater than the circumference around the distal less-rounded apices 404, which is shown most clearly in FIGS. 11-14. In this configuration a solid outer face around an expanded stent 400 would form a frustum of a cone. This configuration may be manufactured in the same manner as the examples described above with reference to FIGS. 4-7 (i.e., producing a stent with a generally uniform outer circumference), with an added step that may include drawing the distal apices 404 into a smaller circumference upon suturing them to a smaller diameter graft material. Alternatively, or in addition, the stent 400 may be heat-set to impose the desired shape.

Figure 13:
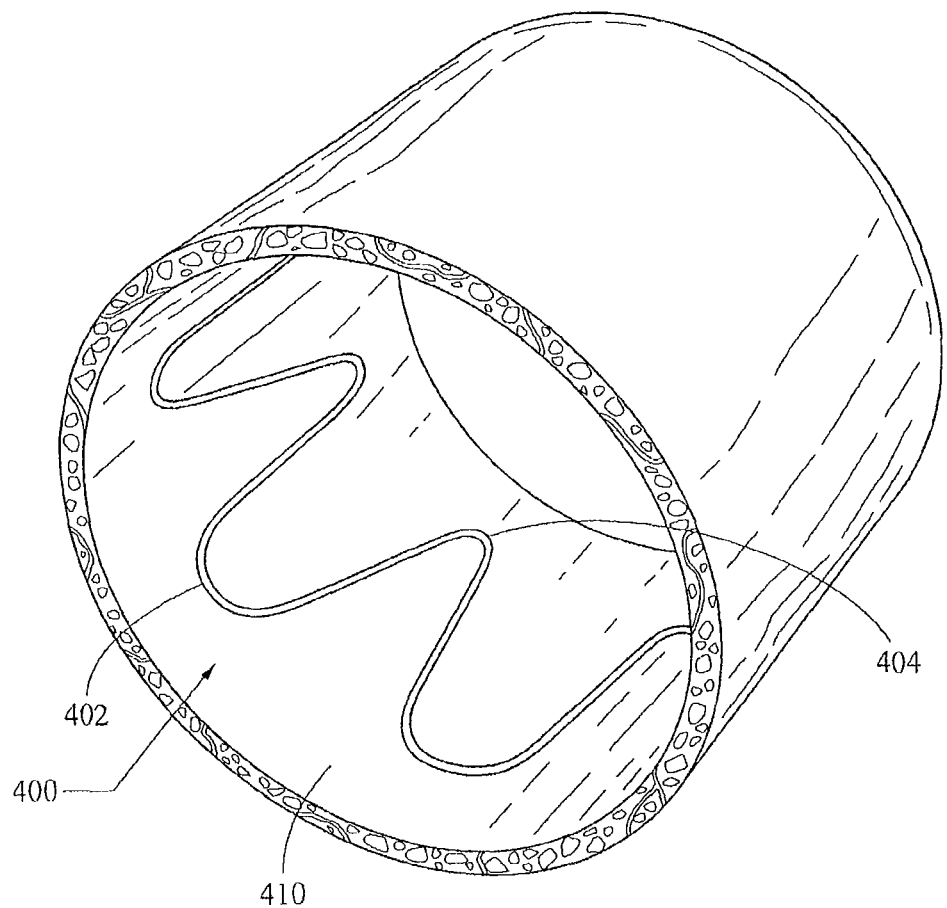
FIG. 13 shows the stent of FIG. 10 in a simulated artery.

FIG. 13 is adapted from an FEA contour simulation and shows the stent 400 in a simulated artery 410, where the stent 400 is 20% oversized. Surprisingly, the contour of pressure distribution along proximal and distal apices 402, 404 as well as an intermediate region is generally uniform throughout the stent circumference. The illustrated configuration provides a total radial sealing force of about 0.187 lbf. This property of generally uniform pressure distribution may provide advantages in certain applications of providing a seal and/or presenting less abrasion of a vessel wall through graft material as compared to stents with less uniform pressure distribution.

Figure 14:
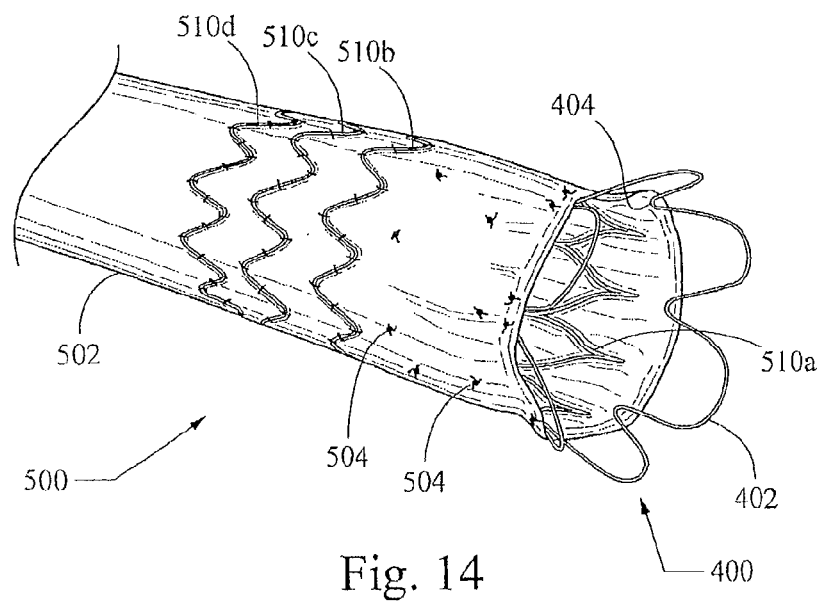
FIG. 14 is a partial perspective of a stent-graft incorporating the stent of FIG. 10.
Figure 15:
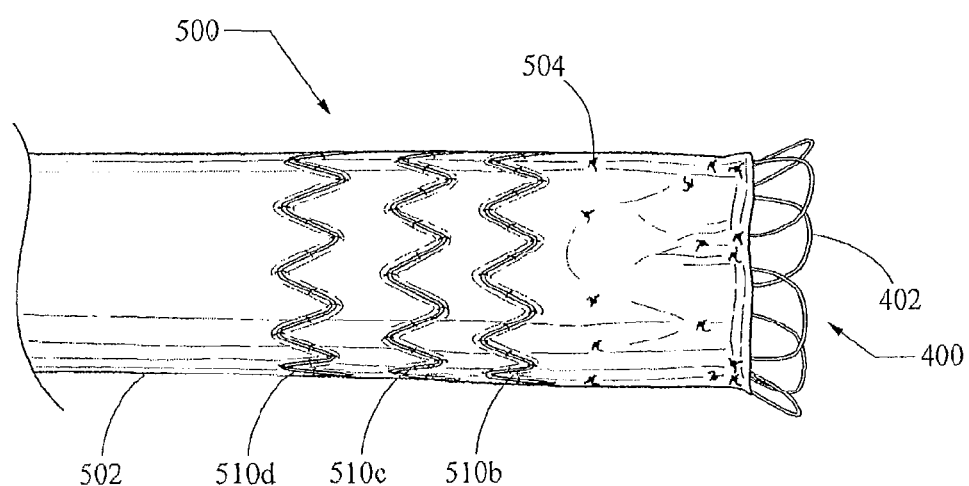
FIG. 15 illustrates a side view of the stent-graft of FIG. 14.

FIGS. 14-15 show two different views of a stent graft 500 using a stent example 400 of the present invention described above with reference to FIGS. 10-13. The stent graft 500 is shown in an expanded state and may be configured for use in treating a thoracic aortic aneurysm. The stent 400 is disposed at the proximal end of a generally cylindrical graft sleeve 502, to which its distal apices 404 are secured by sutures 504. The stent graft 500 also includes a series of z-stents 510a-d disposed distally from the stent 400. The first z-stent 510a is attached to the inner circumference of the graft 502, and the other z-stents 510b-510d are attached to the outer diameter of the graft 502. The proximal end of the stent 400 extends beyond the proximal end of the graft in a manner that may facilitate anchoring the graft in a vessel of a patient (e.g., a blood vessel).

The rounded points on the stent may protrude from the graft material only a small amount as is shown in FIGS. 14-15. In this example, only a small portion of the bare wire will be exposed to the artery wall. These unique (larger radii) rounded points are far less likely to perforate the artery wall than sharper points of a different stent configuration. Advantageously, this asymmetric stent design will maximize the efficacy of the seal while preserving the condition of the artery wall. Specifically, the narrower stent apices will provide for desirable radial expansion/sealing force, and the broader rounded apices will provide for a desirably atraumatic contact with an artery wall.

Figure 16:
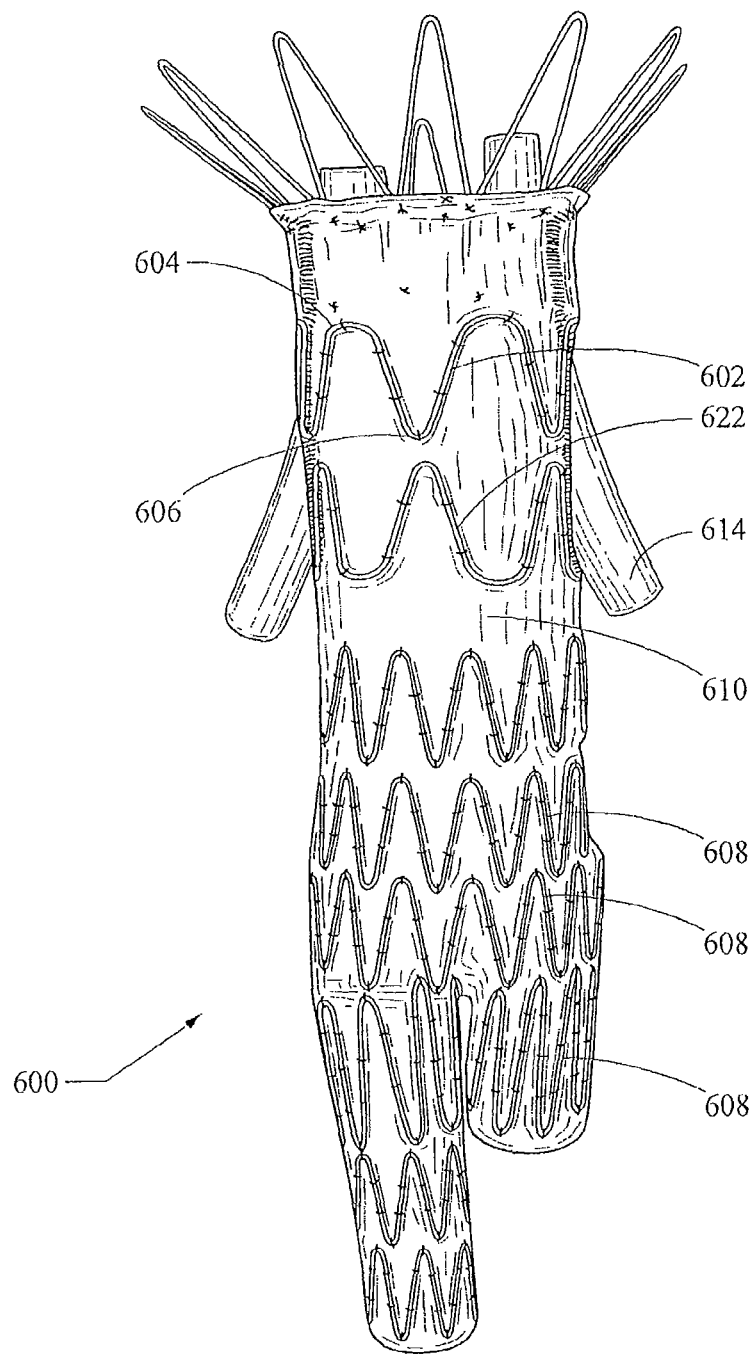
FIGS. 16-18 show a stent-graft with side branches.
Figure 17:
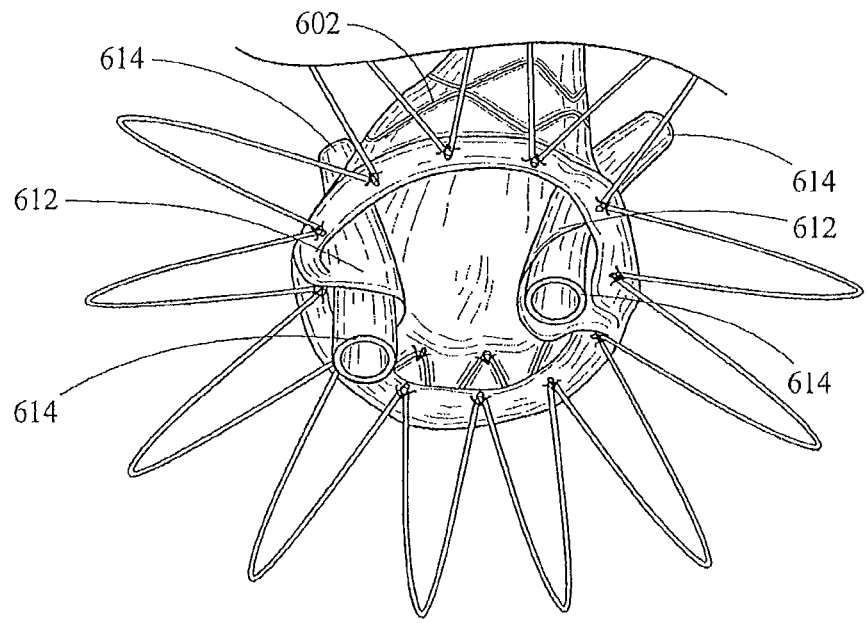
Figure 18:
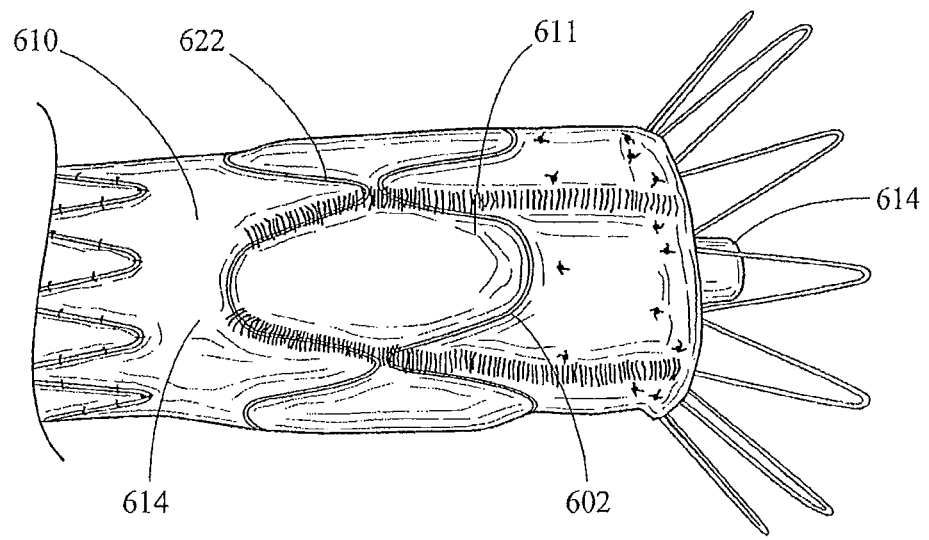

FIGS. 16-18 show a stent-graft embodiment 600 that includes a non-symmetrical stent 602 having more broadly rounded proximal apices 604 and more narrowly rounded distal apices 606. The stent 602 is attached by sutures to the inner surface (not shown) or outer surface of a generally columnar graft 610, which includes other stents 608. A second layer of graft material 612 is also attached to the inner circumference of the graft 610 midway down its length and extends proximally through the inner circumference of the stent 602.

As shown in the end view of FIG. 17, this construction provides a passage for branch structures 614 (that may be embodied, for example, as tubular or non-tubular stents, stent-grafts, shown here for the sake of illustration as generic tubular structures), which pass through the passage formed between the two layers 610, 612 and through an aperture 611 in the graft 610. The tubular structures 614 will advantageously be disposed generally transversely through the inner radius of the more broadly rounded proximal apices 604 of the stent 602, which provides atraumatic columnar support for the graft 610 as well as an anchor for the tubular structures 614. The stent-graft 600 may be particularly useful for treatment of an abdominal aortic aneurysm (AAA) that is immediately adjacent to, or that goes across, the renal arteries such that it has a short neck and lacks a contact area that is sufficient to create an effective proximal seal and avoid the proximal Type I endoleaks that may occur with some currently-available AAA stent-grafts. Those of skill in the art will appreciate that the stent-graft 600 will allow general occlusion of the AAA, while providing patent passage through the descending aorta and from the aorta to the renal arteries. Specifically, a stent-graft configured in the manner of the stent-graft embodiment 600, which includes a modular design that may include branch stents and/or stent-grafts, will allow a seal to be formed above the renal arteries and below the celiac and superior mesenteric arteries. Also, as shown in FIG. 16, a second non-symmetrical stent 622 may be placed adjacent the first non-symmetrical stent 602 in an opposite orientation that will provide additional atraumatic support for the branching tubular structures 614.

Figure 19:
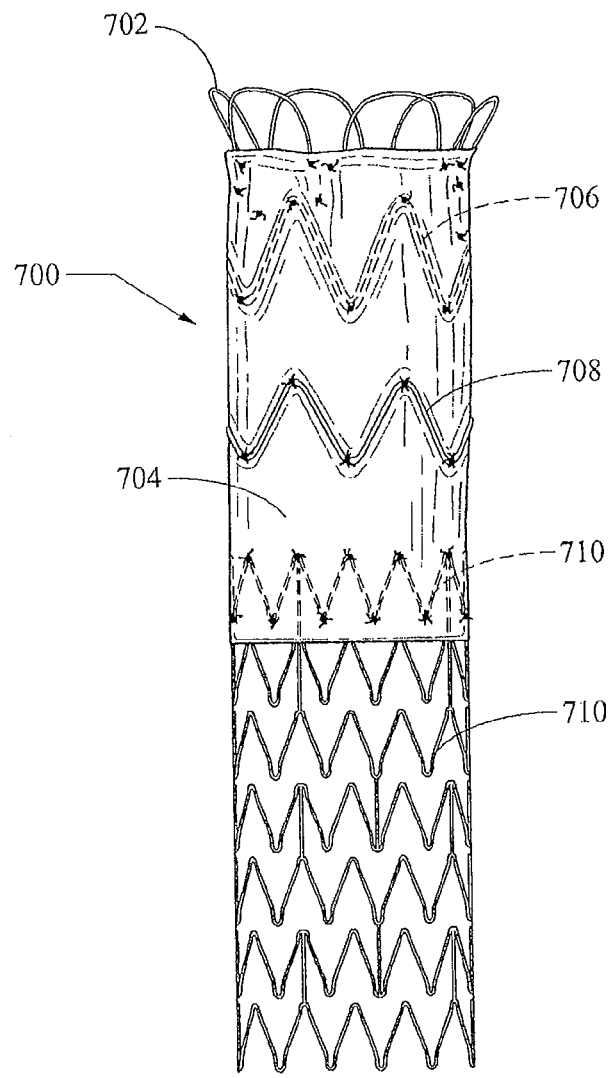
FIG. 19 is a side view of a stent-graft device configured for endovascular treatment of a thoracic aorta dissection.

FIG. 19 shows a stent-graft device 700 configured for endovascular treatment of a thoracic aorta dissection. The device 700 includes a non-symmetrical alignment stent 702 attached to a first end of a tubular graft material 704. A sealing stent 706 is attached in the central lumenal graft space proximate the alignment stent 702. The sealing stent 706 preferably is configured with a high radial force to promote efficacious sealing of the graft material 704 against a vessel wall. A body stent 708 configured here as a z-stent is disposed on the exterior of the graft material 704 and preferably is configured to provide longitudinal and circumferential stability/columnar support for the graft material of the device 700, such that it will conform to the vasculature and resist buckling when deployed in torturous anatomy such as the ascending thoracic aorta. A bare cannula stent 710 (such as, for example, a cut nitinol stent) is attached in the tubular graft material 704 at the opposite end from the alignment stent 702. This cannula stent 710 preferably is a conformable kink-resistant stent that provides distal sealing and migration-resistance. In a deployment of the device 700 to treat an aortic dissection, the alignment stent 702 preferably will be disposed proximal (nearer the heart) relative to the vessel tear, with the graft material traversing the tear in a manner generally sealing it from blood flow. And, the distal cannula stent 710 will help conform to the vasculature and retain a seal for treatment of the dissection. One or more of the sealing stent 706, body stent 708, and bare stent 710 may include one or more barbed projections configured to help anchor the device 700.

Figure 20:
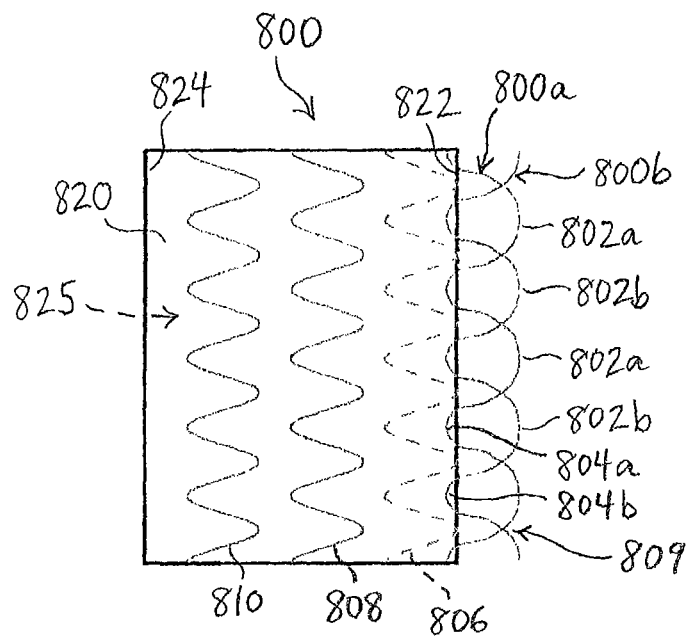
FIGS. 20-21 are, respectively, side and perspective views of a proximal region of an alternative stent-graft.
Figure 21:
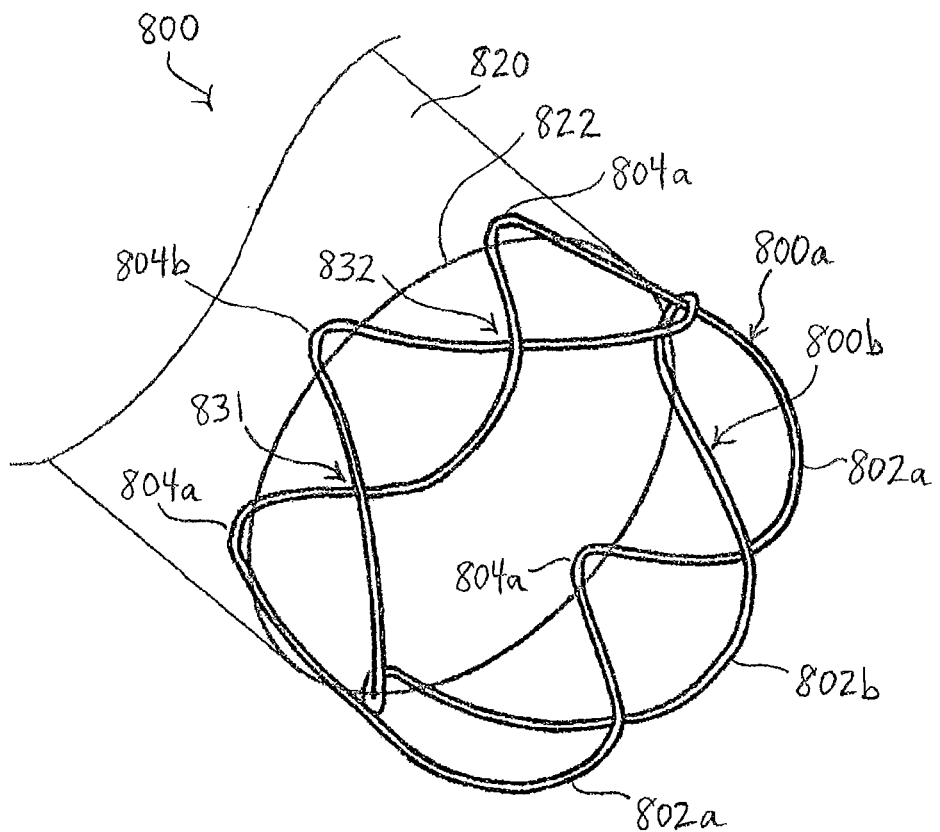

Referring now to FIGS. 20-21, an alternative stent-graft 800 comprises a graft 820 having proximal and distal ends 822 and 824 and a lumen 825 extending therebetween, and also comprises a first stent 800a and a second stent 800b. In this non-limiting embodiment, the first stent 800a comprises a plurality of proximal apices 802a, a plurality of distal apices 804a, and a plurality of generally straight portions disposed between the plurality of proximal and distal apices 802a and 804a. Similarly, the second stent 800b comprises a plurality of proximal apices 802b, a plurality of distal apices 804b, and a plurality of generally straight portions disposed between the plurality of proximal and distal apices 802b and 804b, as shown in FIGS. 20-21.

In one embodiment, the series of distal apices 804a of the first stent 800a are each disposed distal to the proximal end 822 of the graft 820, and the series of proximal apices 802a of the first stent 800a are each disposed proximally beyond the proximal end 822 of the graft 820. Additionally, the series of distal apices 804b of the second stent 800b are each disposed distal to the proximal end 822 of the graft 820, and the series of proximal apices 802b of the second stent 800b are each disposed proximally beyond the proximal end 822 of the graft 820, as shown in the illustrative embodiment of FIGS. 20-21. It should be noted that the series of distal apices 804a and 804b of the first and seconds stents 800a and 800b, respectively, may be coupled to either the inside or outside of the graft 820.

The first stent 800a may comprise a first uniform segment, and the second stent 800b may comprise a second uniform segment, as depicted in FIGS. 20-21. In one example, the first uniform segment of the first stent 800a comprises portions disposed both internal and external to the second uniform segment of the second stent 800b, as noted by overlapping regions 831 and 832 in FIG. 21. The first stent 800a and the second stent 800b may comprise a single filament of wire that is wound into the desired configuration, or may originate from a cannula that is formed, e.g., by laser cutting, into the configuration shown.

In one embodiment, each of the proximal apices 802a of the first stent 800a may be circumferentially offset from each of the proximal apices 802b of the second stent 800b. Further, each of the distal apices 804a of the first stent 800a may be circumferentially offset from each of the distal apices 804b of the second stent 800b.

In one exemplary embodiment, the first stent 800a and the second stent 800b comprise identical geometries. By way of example, and without limitation, the first stent 800a and the second stent 800b may comprise similar features to the stents 200 and 702, described in detail above. In this embodiment, at least one distal apex 804a of the first stent 800a may comprise a first curved portion having a first radius of curvature, e.g., ($r^d$) in the embodiment of FIG. 5 above, and at least one proximal apex 802a of the first stent 800a may comprise a second curved portion having a second radius of curvature, e.g., ($r^p$) in the embodiment of FIG. 5 above, where the second radius of curvature is greater than the first radius of curvature. Similarly, at least one distal apex 804b of the second stent 800b comprises a third curved portion having a third radius of curvature, and at least one proximal apex 802b of the second stent 800b comprises a fourth curved portion having a fourth radius of curvature, where the fourth radius of curvature is greater than the third radius of curvature.

In one embodiment, the dimensions of the third radius of curvature of the second stent 800b may correspond to the dimensions of the of the first radius of curvature of the first stent 800a, while the dimensions of the fourth radius of curvature of the second stent 800b may correspond to the dimensions of the of the second radius of curvature of the first stent 800a. In alternative embodiments, it is contemplated that the first and third radii of curvature may differ relative to each other, and the second and fourth radii of curvature may differ relative to each other.

In the instance in which the first stent 800a and the second stent 800b comprise similar features to the stents 200 and 702 described in detail above, the second radius of curvature of at least one of the proximal apices 802a of the first stent 800a is at least two times greater than the first radius of curvature of at least one of the distal apices 802a. In one example, the first radius of curvature is from about 0.5 mm to about 1.5 mm, while the second radius of curvature is from about 4 mm to about 9 mm. A ratio of the first radius of curvature to the second radius of curvature may be about 1:2.6 to about 1:18.

Advantageously, in the embodiment of FIGS. 20-21, the provision of the first and second stents 800a and 800b in the manner depicted may provide an increased rounded profile at the proximal end that contacts a vessel wall, thereby potentially reducing trauma to a patient's vessel. More specifically, by providing two stents 800a and 800b, each having relatively rounded proximal apices, and arranging them in an out-of-phase alignment, the number of non-contact spaces 809 may be reduced, while rounded regions for atraumatic contact are enhanced.

Notably, if the first and second stents 800a and 800b overlap with one another as shown in FIGS. 20-21, the number of trigger wires does not need to be increased, and in fact may be reduced, since radially restraining one portion of one of the stents 800a or 800b will also radially restrain portions of the other stent. Further, it should be noted that if first and second stents 800a and 800b are used in an overlapping manner, the wires forming the first and second stents 800*a* and 800*b* may comprise smaller cross-sectional areas, and therefore the overall radial profile of the device may not be increased. In certain embodiments, the radial force provided by the first stent 800*a* may be greater or less than the radial force provided by the second stent 800*b*.

In the embodiment of FIGS. 20-21, any number of additional stents, beyond the first and second stents 800*a* and 800*b*, may be used depending on the nature of the condition and bodily passage. In this non-limiting example, the stent-graft 800 comprises a sealing stent 806 attached to the graft 820 within the lumen 825 distal to the proximal end 822 of the graft 820, as shown in FIG. 20 (the sealing stent 806 is omitted for illustrative clarity in FIG. 21). Additional, exemplary stents 808 and 810 are disposed distal to the sealing stent 806, though it will be appreciated that any number of stents may be coupled to the graft 820.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent-graft for use in a medical procedure, the stent-graft comprising:
   a graft having proximal and distal ends and a lumen extending therebetween;
   a first stent comprising a plurality of proximal apices, a plurality of distal apices, and a plurality of intermediate portions disposed between the plurality of proximal and distal apices of the first stent, where the plurality of distal apices of the first stent comprise curved distal apices and are each disposed distal to the proximal end of the graft and overlap with the graft, and where the plurality of proximal apices of the first stent are each disposed proximally beyond the proximal end of the graft; and
   a second stent comprising a plurality of proximal apices, a plurality of distal apices, and a plurality of intermediate portions disposed between the plurality of proximal and distal apices of the second stent, where the plurality of distal apices of the second stent are each disposed distal to the proximal end of the graft and overlap with the graft, and where the plurality of proximal apices of the second stent are each disposed proximally beyond the proximal end of the graft,
   where the first and second stents are at least partially circumferentially out of phase.

2. The stent-graft of claim 1 where the first stent comprises a continuous segment, and the second stent comprises a continuous segment, where the continuous segment of the first stent comprises portions disposed both internal and external to the continuous segment of the second stent.

3. The stent-graft of claim 1 where each of the proximal apices of the first stent is circumferentially offset from each of the proximal apices of the second stent.

4. The stent-graft of claim 1 where each of the distal apices of the first stent is circumferentially offset from each of the distal apices of the second stent.

5. The stent-graft of claim 1 where the first stent and the second stent comprise identical geometries.

6. The stent-graft of claim 1, where at least one distal apex of the first stent comprises a first curved portion having a first radius of curvature, and at least one proximal apex of the first stent comprises a second curved portion having a second radius of curvature, where the second radius of curvature is greater than the first radius of curvature.

7. The stent-graft of claim 6 where the second radius of curvature is at least two times greater than the first radius of curvature.

8. The stent-graft of claim 6 where the first radius of curvature is from about 0.5 mm to about 1.5 mm.

9. The stent-graft of claim 6 where the second radius of curvature is from about 4 mm to about 9 mm.

10. The stent-graft of claim 6 where a ratio of the first radius of curvature to the second radius of curvature is about 1:2.6 to about 1:18.

11. The stent-graft of claim 6 where at least one distal apex of the second stent comprises a third curved portion having a third radius of curvature, and at least one proximal apex of the second stent comprises a fourth curved portion having a fourth radius of curvature, where the fourth radius of curvature is greater than the third radius of curvature.

12. A stent-graft for use in a medical procedure, the stent-graft comprising:
    a graft having proximal and distal ends and a lumen extending therebetween;
    a first stent comprising a plurality of proximal apices, a plurality of distal apices, and a plurality of intermediate portions disposed between the plurality of proximal and distal apices of the first stent, where the plurality of distal apices of the first stent are each disposed distal to the proximal end of the graft and overlap with the graft; and
    a second stent comprising a plurality of proximal apices, a plurality of distal apices, and a plurality of intermediate portions disposed between the plurality of proximal and distal apices of the second stent, where the series of distal apices of the second stent are each disposed distal to the proximal end of the graft and overlap with the graft,
    where the first stent comprises a continuous segment, and the second stent comprises a continuous segment, where the continuous segment of the first stent comprises portions disposed both internal and external to the continuous segment of the second stent.

13. The stent-graft of claim 12, where the series of proximal apices of the first stent are each disposed proximally beyond the proximal end of the graft, and where the series of proximal apices of the second stent are each disposed proximally beyond the proximal end of the graft.

14. The stent-graft of claim 12 where each of the proximal apices of the first stent is circumferentially offset from each of the proximal apices of the second stent.

15. The stent-graft of claim 12 where each of the distal apices of the first stent is circumferentially offset from each of the distal apices of the second stent.

16. The stent-graft of claim 12 where at least one distal apex of the first stent comprises a first curved portion having a first radius of curvature, and at least one proximal apex of the first stent comprises a second curved portion having a second radius of curvature, where the second radius of curvature is greater than the first radius of curvature.

17. A stent-graft for use in a medical procedure, the stent-graft comprising:
    a graft having proximal and distal ends and a lumen extending therebetween;
    a first stent comprising a plurality of proximal apices, a plurality of distal apices, and a plurality of intermediate portions disposed between the plurality of proximal and distal apices of the first stent, where at least one distal apex of the first stent comprises a curved distal apex comprising a first curved portion having a first radius of curvature, where at least one proximal apex of the first stent comprises a second curved portion having a second radius of curvature, where the second radius of curvature is greater than the first radius of curvature; and a second stent comprising a plurality of proximal apices, a plurality of distal apices, and a plurality of intermediate portions disposed between the plurality of proximal and distal apices of the second stent, where at least one distal apex of the second stent comprises a curved distal apex comprising a third curved portion having a third radius of curvature, and at least one proximal apex of the second stent comprises a second curved portion having a fourth radius of curvature, where the fourth radius of curvature is greater than the third radius of curvature, where the first and second stents at least partially overlap relative to one another and where the first stent comprises portions disposed both internal and external to the second stent.

18. The stent-graft of claim 17 where the first stent comprises a continuous segment, and the second stent comprises a continuous segment, where the continuous segment of the first stent comprises portions disposed both internal and external to the continuous segment of the second stent.

19. The stent-graft of claim 17, where the plurality of proximal apices of the first stent are each disposed proximally beyond the proximal end of the graft, and where the plurality of proximal apices of the second stent are each disposed proximally beyond the proximal end of the graft.

20. The stent-graft of claim 17 where each of the proximal apices of the first stent is circumferentially offset from each of the proximal apices of the second stent, and where each of the distal apices of the first stent is circumferentially offset from each of the distal apices of the second stent.

* * * * *